(12) United States Patent
Aysin (10) Patent No.: US 11,408,881 B2
(45) Date of Patent: Aug. 9, 2022

(54) TEST METER AND METHOD FOR DETECTING UNDUE PRESSURE APPLIED TO AN INSERATED TEST STRIP

(71) Applicant: Roche Diabetes Care, Inc., Indianapolis, IN (US)

(72) Inventor: Benhur Aysin, Fishers, IN (US)

(73) Assignee: ROCHE DIABETES CARE, INC., Indianapolis, IN (US)

( * ) Notice: Subject to any disclaimer, the term of this patent is extended or adjusted under 35 U.S.C. 154(b) by 975 days.

(21) Appl. No.: 15/950,401

(22) Filed: Apr. 11, 2018

(65) Prior Publication Data

US 2018/0321178 A1 Nov. 8, 2018

Related U.S. Application Data

(60) Provisional application No. 62/501,399, filed on May 4, 2017.

(51) Int. Cl.
*G01N 27/327* (2006.01)
*G01N 33/487* (2006.01)

(52) U.S. Cl.
CPC ... *G01N 33/48785* (2013.01); *G01N 27/3273* (2013.01); *G01N 27/3274* (2013.01)

(58) Field of Classification Search
None
See application file for complete search history.

(56) References Cited

U.S. PATENT DOCUMENTS

| | | | |
|---|---|---|---|
| 4,999,582 A * | 3/1991 | Parks | G01N 27/3273 324/692 |
| 6,506,168 B1 * | 1/2003 | Fathallah | A61B 5/150022 600/578 |
| 10,029,252 B2 * | 7/2018 | Hiller | G01N 21/77 |
| 10,485,937 B2 * | 11/2019 | Yodfat | A61M 5/14248 |
| 10,509,004 B2 * | 12/2019 | Harttig | C23C 14/042 |
| 2002/0168290 A1 * | 11/2002 | Yuzhakov | A61B 5/14532 600/583 |

(Continued)

FOREIGN PATENT DOCUMENTS

| | | |
|---|---|---|
| EP | 2 181 651 A1 | 5/2010 |
| EP | 2 693 208 A1 | 2/2014 |
| WO | WO 2010/049669 A1 | 5/2010 |

*Primary Examiner* — Peter J MacChiarolo
*Assistant Examiner* — Mohammed E Keramet-Amircolai
(74) *Attorney, Agent, or Firm* — Woodard, Emhardt, Henry, Reeves & Wagner, LLP (57) ABSTRACT

A test meter and method for detecting the presence and/or concentration of an analyte in a liquid biological sample. The meter includes an internal cavity receiving a test strip. A pressure sensor is arranged and configured to sense a pressure exerted by the inserted test strip relative to the meter housing. A controller receives signals corresponding to the sensed pressure, compares the signal to a pressure threshold value, and indicates when the sensed pressure exceeds the pressure threshold value. The method is for detecting the application of an undue pressure applied against a test strip relative to a meter, and includes receiving a test strip in a meter in a position adjacent a pressure sensor, using the sensor to sense the pressure applied by the inserted test strip relative to the meter, and comparing the sensed pressure to a predetermined threshold value.

23 Claims, 4 Drawing Sheets

(56) References Cited

U.S. PATENT DOCUMENTS

| | | | | |
|---|---|---|---|---|
| 2003/0203498 A1* | 10/2003 | Neel | ................. | G01N 27/3272 436/95 |
| 2003/0212344 A1* | 11/2003 | Yuzhakov | ........... | A61B 5/15117 600/583 |
| 2009/0301899 A1* | 12/2009 | Hodges | .............. | G01N 27/3274 205/782 |
| 2010/0021342 A1* | 1/2010 | Joseph | ............... | A61B 10/0045 422/400 |
| 2012/0010489 A1* | 1/2012 | Miltner | ........... | G01N 35/00009 600/365 |
| 2012/0312699 A1* | 12/2012 | Webster | ............. | G01N 27/3273 205/792 |
| 2013/0034664 A1* | 2/2013 | Forrow | .................. | C12Q 1/001 427/58 |
| 2013/0343964 A1* | 12/2013 | Dreibholz | ........... | G01N 21/78 422/428 |
| 2014/0017123 A1* | 1/2014 | Babic | ............... | A61B 5/150435 422/68.1 |
| 2014/0083872 A1* | 3/2014 | Fuerst | ................ | G01N 27/4145 205/792 |
| 2014/0174947 A1* | 6/2014 | Moffat | ............... | G01N 27/3272 205/777.5 |
| 2014/0255962 A1* | 9/2014 | Rueckert | .................. | C12Q 1/32 436/95 |
| 2014/0273549 A1* | 9/2014 | Sauers | ............... | H01R 13/7039 439/62 |
| 2014/0318991 A1* | 10/2014 | Celentano | ............ | G01N 27/327 205/792 |
| 2015/0076010 A1* | 3/2015 | Austera | ............ | G01N 33/48771 205/792 |
| 2015/0352296 A1* | 12/2015 | Yodfat | ................... | G16H 20/13 604/506 |
| 2016/0003764 A1* | 1/2016 | Beaty, Jr | ............ | G01N 27/3274 205/777.5 |
| 2016/0011178 A1* | 1/2016 | Hoenes | ................. | G01N 21/75 436/95 |
| 2016/0082434 A1* | 3/2016 | Hiller | ................ | B01L 3/502707 422/412 |
| 2016/0143568 A1* | 5/2016 | List | .................. | A61B 5/150068 600/583 |
| 2016/0305899 A1* | 10/2016 | Harttig | ................. | C23C 14/165 |
| 2017/0020424 A1* | 1/2017 | Holweg | ........... | G01N 33/48792 |

\* cited by examiner

TEST METER AND METHOD FOR DETECTING UNDUE PRESSURE APPLIED TO AN INSERATED TEST STRIP

CROSS-REFERENCE TO RELATED APPLICATION

This application claims the benefit of U.S. Provisional Application No. 62/501,399 filed May 4, 2017, which is hereby incorporated by reference.

BACKGROUND

The operation of conventional test strip meters is well known. A test strip is inserted into the meter to a testing position. The user provides a liquid, biological test sample to a sample chamber defined by the test strip. A reaction occurs between an analyte of interest in the sample and a reagent in the sample chamber to generate a measurable result, e.g., optical or electrical, which is assessed by the meter to determine the presence or concentration of the analyte.

There are many features in an analyte strip meter to catch test strip errors before and after dosing. Pre-dose checks are designed to check strip integrity as the first layer of checks. Then there are post-dose checks as the second layer of checks. Although pre- and post-dose checks catch a number of potential error sources, there are still some that can be missed and those can have an impact on the measurement if not corrected for or avoided by some other means.

Failsafes, for example, are designed to perform a variety of integrity checks to detect conditions that would lead to a faulty analyte reading. If a failsafe is triggered, an error code identifying the failsafe, rather than an analyte reading, is displayed by the meter. If a faulty analyte value is not caught by the checks, then additional failsafe algorithms may be designed and implemented to catch them by complicated correction methods. Failsafes are the last layer in catching and/or correcting faulty readings and they get to do most of the work in terms of preventing inaccurate readings which, in the context of healthcare, may give rise to certain health risks. Therefore, accurate detection of faulty readings by failsafes is extremely important as the last layer of safety.

Failsafes may be quite complex and involve advanced algorithms to correct a measurement or to detect if a reading is faulty or not. Algorithms use values derived from electrical or optical signals created by the chemical reaction between reagent and test sample, and extract information to make a decision whether an analyte reading is good or bad. If failsafe algorithms determine that it is a faulty reading or determine that a signal interferent is present, then no analyte value is displayed by the meter or a corrected value is calculated. The issue is that a faulty reading can be caused by many different factors. Designing a comprehensive failsafe algorithm to consider all these different factors and come up with an accurate detection can be a difficult task. If some factors can be eliminated from those which the failsafe has to deal with, then the failsafes will have improved accuracy. With the failsafe being more accurate, it also means that false negatives can be reduced.

The user's dosing technique when applying blood to a test strip can be most influenced by the manufacturer by intuitive design and proper instruction. While the manufacturer is still not able to entirely control dosing technique, monitoring use cases of dosing technique enables a determination of the sufficiency or deficiency of certain techniques, and designing systems and generating instructions aimed at failsafing against deficient techniques. One of the main issues confronted in developing failsafes for an analyte test strip meter and a test strip inserted in such meter is to distinguish dosing techniques that may produce biased test results (outliers). The manner in which the user doses a test strip can affect the response. A user should normally dose the strip by lightly touching the blood drop to the end of the strip. However, a person may instead push on the test strip with a lot of pressure while dosing the strip, whether voluntarily or involuntarily. A person may also push the strip up or down, or side to side, causing the strip to bend. All of these applications of undue pressure can cause significantly biased test results.

Outliers caused by applying undue strip pressure are particularly troublesome, and increase the risk of the user relying on inaccurate test results. Adding to the difficulty in detecting bias caused by such a strip-perturbing dosing technique is the fact that in many instances the signals generated from the reaction between the sample and reagent appear to be within the normal tolerance range for a useful measurement.

SUMMARY OF THE INVENTION

One or more pressure sensors are implemented in a strip meter to sense the pressure profile applied by a user on a test strip during insertion, during sample dosing, and during the measurement sequence. The meter uses the sensor to detect a pressure applied to the test strip. If this pressure exceeds a pre-determined pressure threshold or profile criteria, then the test may be aborted. The meter is thereby able to detect and prevent inaccurate readings. This can also lessen the burden on failsafe algorithms which may otherwise need to be designed to account for potential errors from poor dosing technique and thereby add to the complexity of the algorithms. By lessening the complexity by relieving the algorithms of this further burden, the algorithms can do a better job catching and/or correcting for other sources of error.

It is an object of the present invention to provide a strip meter and related method for identifying and reporting biases due to improper dosing technique when a person applies an undue pressure or pressure profile on a test strip.

It is another object of the present invention to reduce the incidence and associated risks of patients relying on erroneous test strip results.

A further object is to add an important extra layer of protection in preventing biased readings.

It is a further object of the present invention to employ and implement sensors in a meter that can not only sense how hard a test strip is pushed but also differentiate different types of pressure, stress, and/or movement exerted on the test strip in order to compare to a corresponding predetermined threshold for the determined type, so as to abort a test when appropriate.

Another object is to detect the amount of perturbation and, rather than abort the test, determine and implement an appropriate correction technique distinct from the primary measurement algorithm in order to correct for the perturbation in a manner that avoids adding to the complexity of the primary measurement algorithm.

The present invention also lessens the burden on failsafe algorithms so that they can deal with other kinds of failure modes, thereby providing more efficient failsafe algorithms and safer systems.

DETAILED DESCRIPTION OF THE ILLUSTRATED EMBODIMENTS

For the purposes of promoting an understanding of the principles of the invention, reference will now be made to the selected embodiments illustrated in the drawings and specific language will be used to describe the same. It will nevertheless be understood that no limitation of the scope of the invention is hereby intended, such alterations, modifications, and further applications of the principles of the invention being contemplated as would normally occur to one skilled in the art to which the invention relates. At least one embodiment of the invention is shown in great detail, and it will be apparent to those skilled in the relevant art that some features or some combinations of features may not be shown for the sake of clarity.

The present invention relates to improved systems and methods for detecting an analyte presence or concentration by use of a test strip or analytical test field provided on a substrate. For purposes herein, the present invention is described in connection with a meter operating an electrochemical testing system. It will be appreciated, however, that the invention is equally useful in connection with alternative types of strip testing systems, e.g., colorimetric, photometric, and the like, as well as systems comprising test strips having a single test field or spooled tapes having multiple test fields provided seriatim. The invention has utility in any such test system in which it is desired to determine if undue pressure, forces, or other perturbation has been applied to the test strip. Similarly, the invention is described herein with respect to an end dosing test strip. However, test strips which are dosed at the side or top are also susceptible to providing incorrect results if undue pressure is applied, and the invention is therefore also applicable thereto.

Figure 1:
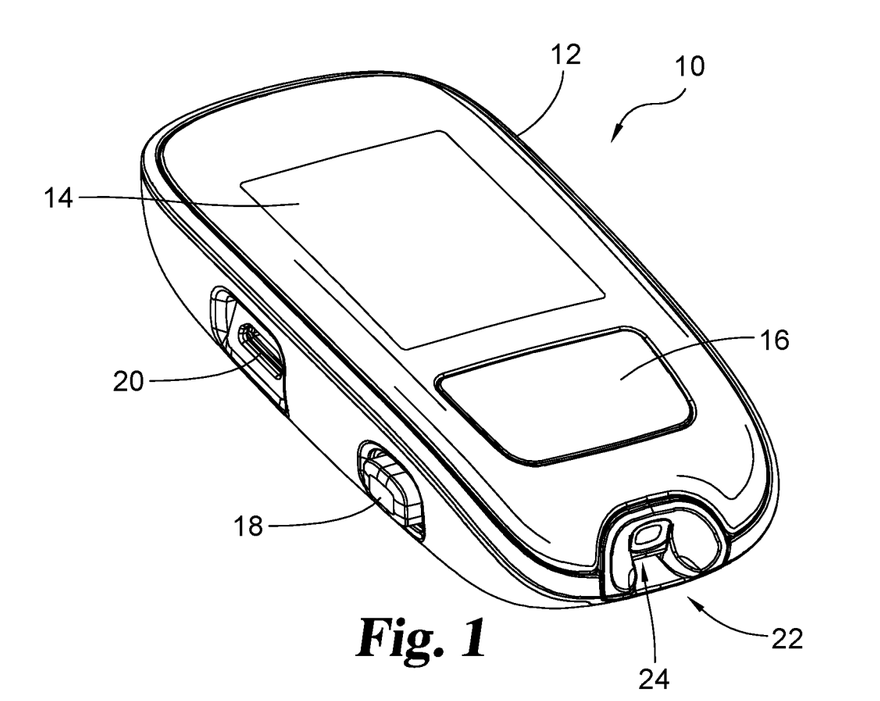
FIG. 1 is a perspective view of an exemplary meter configured to detect undue pressure on an inserted test strip.
Figure 2:
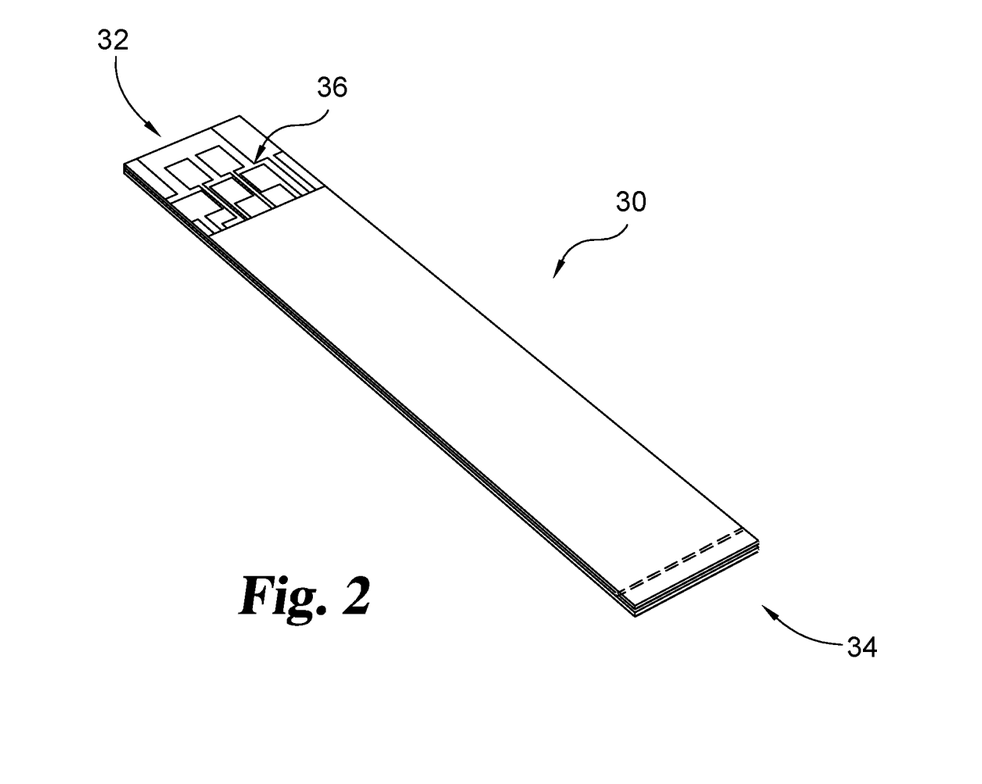
FIG. 2 is a perspective view of an illustrative test strip for use with the meter of FIG. 1.
Figure 3:
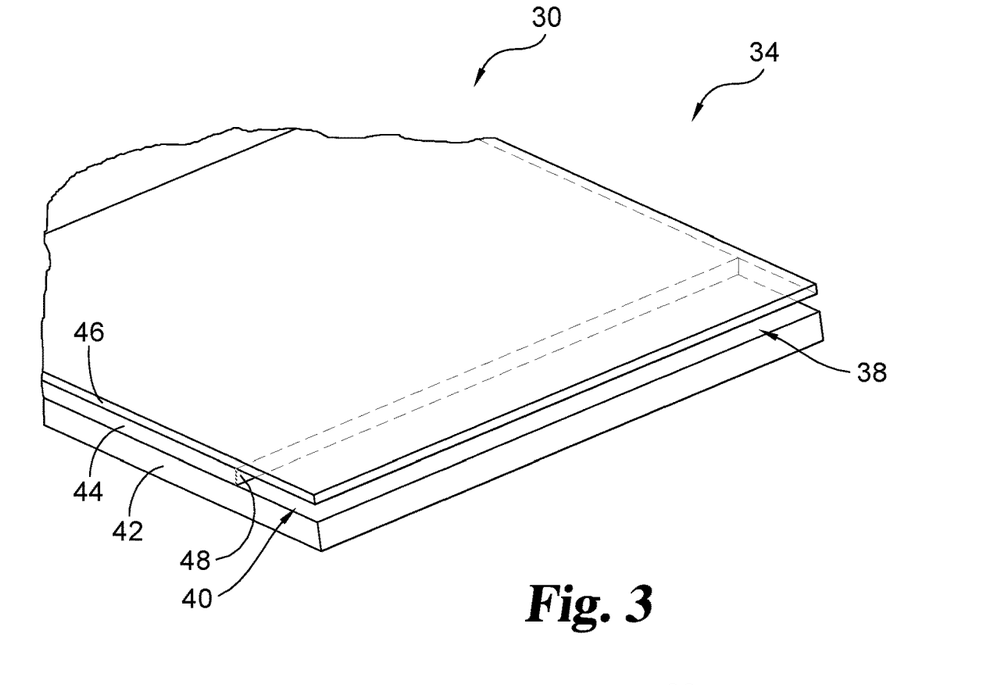
FIG. 3 is a perspective view of a sampling end of the test strip of FIG. 2.
Figure 4:
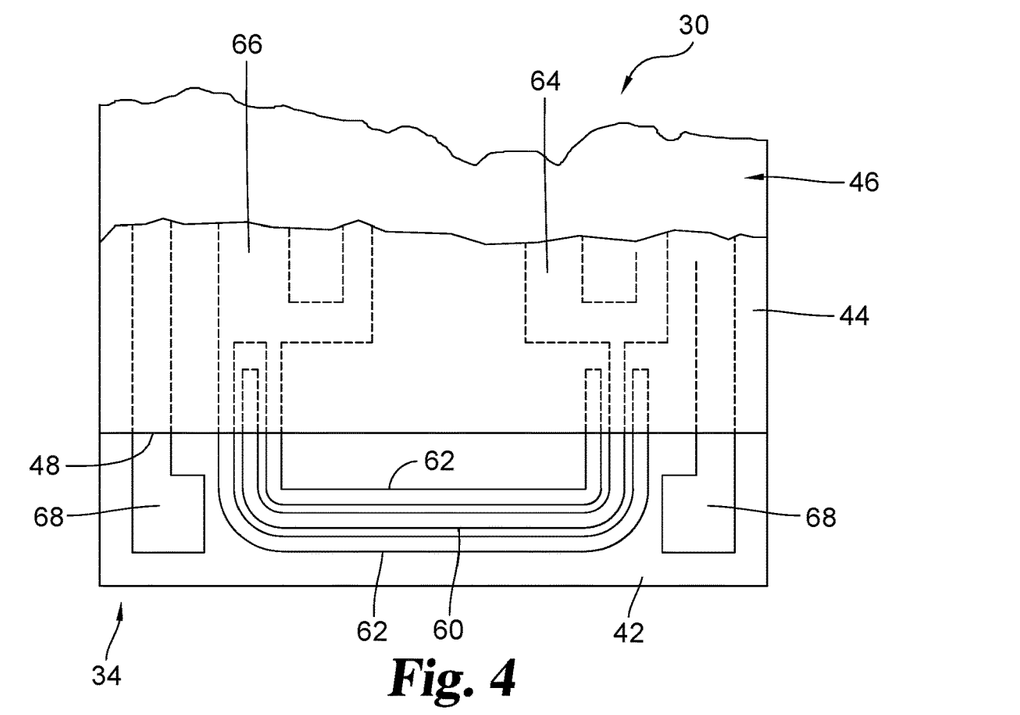
FIG. 4 is a top plan view in partial cut-away showing the sampling end of the test strip of FIG. 2.

Referring to FIG. 1 there is shown an exemplary meter 10 including a housing 12 containing various meter components such as a power supply, processor, memory, controller and the like. As illustrated, housing 12 carries an external display 14, input control 16, strip ejection button 18 (for activating a strip eject mechanism within the housing, if provided) and data communication port 20. Housing 12 includes a strip port 22 comprising port opening 24 communicating with an internal cavity which is sized and shaped to receive at least a portion of a complementary test strip 26, aspects of which are shown in FIGS. 2-4.

Test strip 30 generally comprises a flat, elongated, narrow strip having a meter connection end 32 and a sample end 34. Meter connection end 32 comprises a plurality of contact pads 36 configured for making electrical contact with meter contacts within the housing when the meter connection end 36 of the test strip is received through port opening 24. As shown in FIG. 3, sample end 34 is configured to provide an inlet 38 leading to a capillary sample chamber 40 to receive a blood or other liquid sample for testing. In one embodiment, for example, test strip 30 comprises a three-layer laminate structure including base 42, spacer 44 and top 46. The base and top extend lengthwise beyond the end 48 of spacer 44 to form sample chamber 40. The spacer is sized such that dosing a liquid sample to inlet 38 of sample chamber 40 results in a capillary flow of the liquid to fill the chamber 40. As will be appreciated by those of ordinary skill in the art, other sample chamber structures are also known and are suitable for use in the context of the present invention.

In the provided example of an electrochemical test strip, sample chamber 40 includes working electrode 60 and counter electrodes 62. These electrodes are connected by traces 64 and 66, respectively, to associated contact pads 36 at meter connection end 32 of strip 30. A reagent (not shown) is positioned adjacent at least to the working electrode but may be positioned adjacent both the working and the counter electrodes. In conventional fashion for conducting an electrochemical analysis, a potential is applied across the working and counter electrodes at a time when the sample liquid bridges the gap between the electrodes. The measurement sequence including this potential application can be programmed to begin after one or both of a dose detection and dose sufficiency technique utilizing a combination of the working and counter electrodes as well as optionally provided dose sufficiency electrodes 68. The analyte of interest in the liquid sample reacts with the reagent and, e.g., a resulting current across the electrodes is measured as one basis for determining the presence and/or concentration of the analyte.

The present invention involves the determination of pressure applied by a user to sample end 34 which might affect the accuracy of the test. In particular, the present invention provides for the detection of undue pressure which could be associated with a distortion of the test strip in a manner which would adversely affect the test results.

The sample chamber of a test strip is susceptible to distortion based on pressure applied to the sample end of the test strip which can be particularly problematic if this occurs during the measurement sequence. Test strips are typically mass produced using materials which have some amount of flexibility which facilitates fabrication. While test strips have adequate integrity in normal use, it is possible for a user to apply undue pressure to the sample end. As used herein, the term "undue pressure" indicates an amount of pressure which may result in an erroneous determination as to the presence and/or concentration of analyte in a test sample. As hereafter discussed, a pressure may be undue in view of a variety of factors, including the type of pressure, the direction of pressure, and the time and/or duration of the pressure.

Test strips typically operate using very small volumes of the test sample. The sample chambers thus have correspondingly small dimensions, and the components are relatively thin. The sample chambers, or at least pathways leading thereto, are positioned relatively close to the sample end of the test strip. Undue pressure applied to the sample end of the test strip can therefore easily distort the size and/or shape of the sample chamber. This in turn may have a significant effect on the accuracy of the test if the conditions for generating the analyte-specific current are affected. As used herein, the terms "distortion" or "distorting" are used to refer to a change in a test strip which results from the application of undue pressure at the sample end of the test strip. In an alternative theory, undue pressure applied to the sample end during a measurement sequence may cause distortion or short-duration disconnection of the electrical contact between the meter contacts and the contact pads of the test strip. The present invention is believed to address the resulting problem under any theory for how accuracy is impacted as a result of undue pressure being applied to any portion of the test strip including the sample receiving end.

Distortions of the sample chamber and associated pathways may impact the flow of test sample to the sample chamber, the mixing and "settling down" of the test sample with the reagent, the relationship between electrodes or other detecting elements in the chamber, and other aspects of the testing system. In the extreme, undue pressure may also affect the integrity of the electrodes or other detecting elements. The usefulness of test strips is premised on the calibration of a test strip system based on optimization and/or uniformity of operating conditions for measurement, in terms of volumes, sample movement, and detection systems, among other things. Detecting undue pressure can identify whether an erroneous reading may result from a distortion of the test strip.

Figure 5:
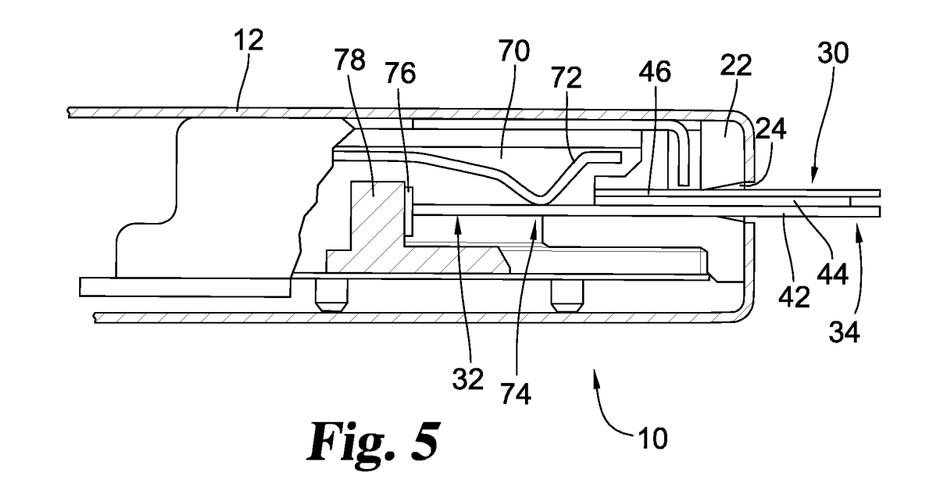
FIG. 5 is a side, elevational view, in partial cross section, showing the test strip of FIG. 2 received in the meter of FIG. 1 in accordance with an embodiment described herein.

Referring to FIG. 5, there is shown a test strip 30 with its meter connection end 32 fully inserted into housing cavity 70 through opening 24 to a testing position within meter 10. In this testing position, sample end 34 extends outwardly of the meter. As fully inserted, meter contacts 72 are received in contact with respective contact pads 36, such as at location 74, on base 42 of test trip 30. The contacts 72 are in electrical communication with meter circuitry which is configured to operate with the test strip to conduct an analyte test. With insertion, test strip 30 in this embodiment is received with its meter connection end 32 adjacent a pressure sensor 76 supported on end wall 78 of housing 12. In the optimal testing position, the meter connection end 32 of the test strip rests adjacent to the sensor 76 with no or limited pressure being further applied once in the testing position.

In conducting a test, test strip 30 is inserted into the testing position as shown in FIG. 5. Meter 10 may be activated in a variety of ways, such as by a manual switch or automatically as a result of a detection of the strip insertion. Once so activated, the meter conducts initial checks regarding viability of the test strip for testing. This may include, for example, checking for current leaks, circuit faults, and the like. Once the initial checks have been completed and the test strip has been found to be acceptable to initiate a test, the meter signals the user to dose the strip with a test sample. Thereafter, the user contacts the sample chamber inlet 38 of the test strip with the test sample. This will involve contacting inlet 38 with a drop of the test sample, typically while the drop resides on the user's finger or other skin surface (after lancing). In accordance with the present invention, the pressure applied against the test strip is monitored after the meter activation for the presence of undue pressure during some or all of the time from insertion of the test strip to completion of the test.

The present invention involves the use of one or more pressure sensors arranged and configured in the meter in a way that the sensors detect the pressure applied to a test strip by sensing that pressure relative to the meter. The purpose of the sensor is to determine the amount of pressure applied to the dosing end of the test strip, particularly after dosing a sample and during the measurement sequence. In one embodiment, shown in FIG. 5, the sensor detects pressure exerted against the test strip in the lengthwise direction, longitudinally of the strip cavity. This pressure may result from inserting the test strip, dosing the strip with the sample fluid, or from other actions such as accidental contact with the test strip during a measurement sequence after dosing. Pressure applied to the test strip in this manner may have the effect of distorting the test strip, disturbing the sample/reagent kinetics, or disrupting the electrical connection between the strip and the meter.

As shown in FIG. 5, pressure sensor 76 is positioned between the meter connection end 32 of test strip 30 and wall 78. Sensor 76 is operable to detect pressure exerted by test strip 30 relative to wall 78 of housing 12. The sensor is thereby arranged and configured to sense a pressure transmitted through the test strip from the sample end 34 of the test strip relative to meter 10. This "End Pressure" in turn reflects the amount of pressure, and perhaps undue pressure, applied by the user to the sample end 34 of the test strip.

Figure 6:
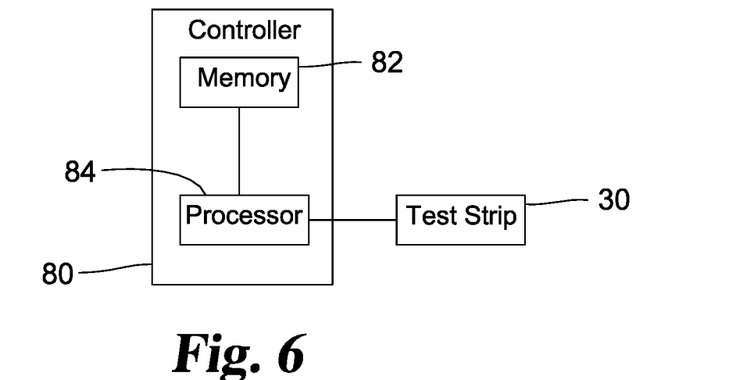
FIG. 6 is a diagram of a controller configured to operate on a test strip in the manner described herein.

Referring to FIG. 6, meter 10 further includes a controller 80 comprising memory 82 and a processor 84. Memory 82 is configured to store one or more predetermined pressure threshold values. Processor 84 is responsive to pressure sensor 76 and is configured to compare sensed pressures to the threshold values. In particular, pressure sensor 76 is configured to generate and transmit to processor 84 a pressure signal indicative of the sensed pressure. Processor 84 is configured to receive the pressure signal and to compare the sensed pressure to a stored pressure threshold value. A person of ordinary skill will understand and appreciate that in the context of electronic devices, stored values may be the actual pressure values or the electrical signal corresponding to such values in order to avoid computational efforts relating to conversion of a signal to a corresponding 'value' and vice versa. In this description, the terms pressure values and pressure signals or a pressure profile (i.e. an indication of the variation of applied pressure over time, or the area under a pressure vs. time profile) may be used interchangeably but are understood and intended to relate to the pressure concept generally, while its actual context is easily discernible herefrom.

Further, processor 84 is configured to indicate when the sensed pressure exceeds the compared pressure threshold value. In response to the sensed pressure value, processor 84 determines a condition indicated by the sensed pressure and transmits a condition signal to controller 80. Controller 80 then provides an output based on the indicated condition. Meter 10 further includes a controller, which may be the same as controller 80, which is configured to detect the presence and/or measure the concentration of an analyte in the biological test liquid.

By way of example, memory 82 may include an End Pressure Max representing the highest pressure that is allowed before it is considered to be undue pressure. This End Pressure Max is the pressure which will be flagged if it is achieved at any time while the test strip is within the meter and the pressure is being monitored. The result of the flagging will vary with the situation, as later described. The point is that sensor 76 operates to monitor the End Pressure at selected times in order to identify the existence of an undue End Pressure.

Figure 7:
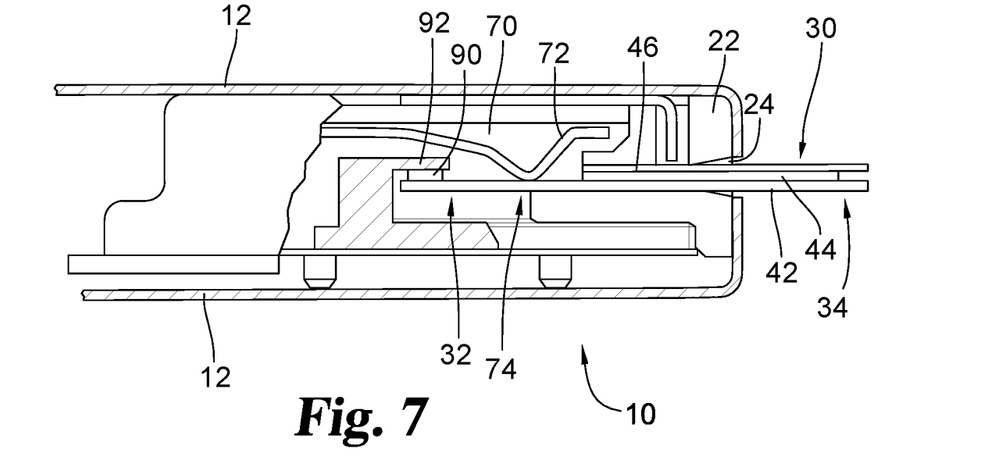
FIG. 7 is a side, elevational view, in partial cross section, showing the test strip of FIG. 2 received in the meter of FIG. 1 in accordance with an alternate embodiment described herein.

The illustrated embodiment includes a pressure sensor positioned to receive pressure applied by the test strip relative to the meter in a direction along the length of the test strip. As described, a distorting pressure may also be applied in other directions, such as by urging the sample end in a direction orthogonal to the length of the test strip, i.e., up, down or to either side. For example, urging the sample end of the test strip up or down will have a tendency to bend the flat test strip. Any such pressure may distort the sample end, particularly if the pressure is applied at the tip of the sample end where the inlet 38 and sample chamber 40 are located, and may even be directly contacted. It is therefore contemplated that in alternate embodiments the present invention provides one or more pressure sensors within the cavity 70 to sense pressures applied in any direction to the sample end of a test strip. For example, shown in FIG. 7 is an embodiment having a pressure sensor 90 located on a housing wall 92 above or below (not shown) the meter end of the test strip in position to sense pressure exerted by the test strip relative to the meter in an upward (or downward) direction.

The meter and related method provide for the detection of pressure exerted by an inserted test strip relative to the meter housing. The detected pressure is compared to one or more predetermined pressure threshold values. These pressure threshold values may be established for pressure in any direction, including lengthwise of the test strip, orthogonal to the strip, or combinations thereof.

In another aspect, the present invention may include any combination of sensors to detect pressure along various directions. For example, an end sensor 76 may be used in combination with top and bottom sensors 90 to detect pressure applied in multiple directions.

Figure 8:
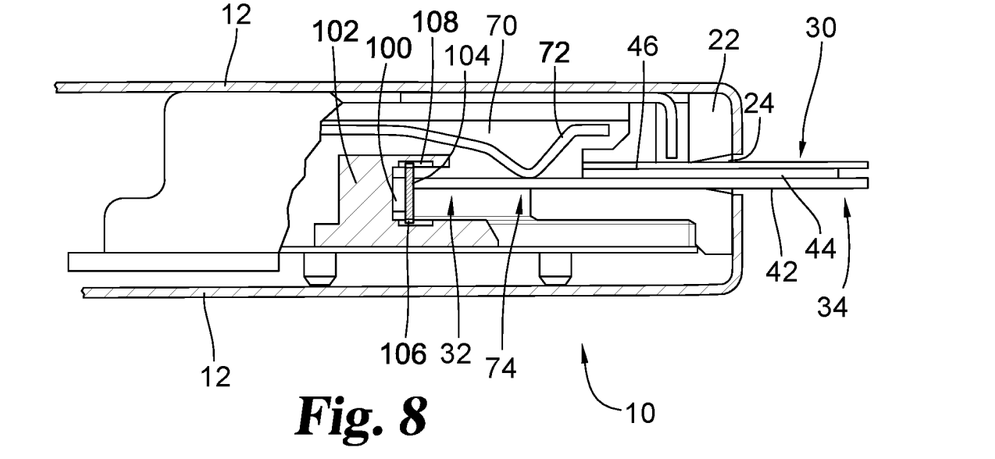
FIG. 8 is a side, elevational view, in partial cross section, showing the test strip of FIG. 2 received in the meter of FIG. 1 in accordance with yet another embodiment described herein.

It will be appreciated that the pressure sensor may be positioned in various ways while still being able to sense pressures applied to the sample end of the test strip. Referring to FIG. 8, the meter 10 is shown to include a partition between an inserted test strip and the pressure sensor. Pressure sensor 100 is positioned on support wall 102, and a moveable wall 104 is positioned in front of sensor 100. Moveable wall 104 includes tabs 106 received within slots 108 and is therefore slideable relative to support wall 102. In this embodiment, the meter end of test strip 30 does not bear directly on pressure sensor 100, but rather the sensor detects the movement of moveable wall 104 as an indication of pressure being applied to the test strip. In another embodiment, the test strip is received within a carriage which moves relative to the meter. This eliminates the repeated contact of test strips directly with the pressure sensor, which over time may damage the sensor.

Undue pressure may be applied to a test strip at various times while the strip is in the meter. The controller and processor are useful to monitor the application of pressure relative to the meter during any of these times. For example, a user may apply undue pressure to the sample end of a test strip during the Insertion Period—the time period while the test strip is being inserted into its testing position and prior to dosing of the strip with the test sample. Undue pressure may also be applied to the sample end during the Dosing Period—the time after the meter has initiated a test and the test sample is applied to the test strip. This will typically occur as the user attempts to place the test sample against the inlet to the sample chamber. Finally, an undue pressure may be applied during the Testing Period—the time after dosing the strip and up until the test results have been obtained (although not necessarily displayed). This may occur, for example, by accidental contact with the test strip, or by prolonged contact by a user after the Dosing Period without removing the finger or other body location from which the sample is provided. If any undue pressure is applied prior to conclusion of the test, it can be noted.

In one aspect, the pressure is sensed over a predetermined period of time, and the processor is configured to indicate if the sensed pressure ever exceeds the pressure threshold during the predetermined period of time. It is therefore an aspect of the present invention that monitoring the test strip pressure is performed during any or all of the Insertion Period, the Dosing Period and the Testing Period. Pressure monitoring during the Insertion Period may detect improper handling of the test strip which may damage the sample chamber, and which is not otherwise caught by other pre-dose checks. Pressure monitoring during the Dosing Period will be particularly suited to detect pressures that may affect the flow of the test sample or the mixing or reaction kinetics between the sample and reagent. Pressure monitoring during the Testing Period will be able to identify pressures which may adversely affect the processing that occurs as the analyte is being detected.

It will be appreciated that the significance of an amount of pressure applied to the test strip may vary depending on when it is applied. For example, pressures which may affect the flow of the test sample (during the Dosing Period) or the analysis of the test sample (during the Testing Period) may not have the same significance if applied during the Insertion Period. It is therefore a feature of the present invention to provide threshold pressure values which correlate to the time the pressure is applied relative to the different periods, and the timing within each period, of the test procedure.

The duration of an applied pressure may also be significant. For an excessively high pressure, even an instantaneous application of the pressure may be significant if the damage will have occurred quickly. However, in other circumstances a given pressure may not be significant unless it has occurred for a sufficient length of time to adversely affect the test. It is therefore an aspect of the present invention to provide threshold values which reflect the combined effect of the amount of a sensed pressure and the duration of that pressure. Moreover, it is an aspect that threshold pressures may further take into account the amount of the pressure, the duration of the pressure, and the time during which it occurs.

The sensed pressure may be of several types. For example, the pressure may be a relatively brief or instantaneous pressure, or it may be a sustained pressure. The pressure may also vary in amount over time, either in a regular or irregular fashion.

One type of pressure is one which reaches a predetermined amount which is considered a "not to exceed" pressure. As indicated, this pressure may vary for a system depending on when the pressure is applied. In one embodiment of the present invention, the threshold values include an Absolute Pressure Max which is considered to be the pressure which, if reached at any time, is considered to indicate that the test strip is not usable for testing. In other embodiments, a separate Absolute Pressure Max may be assigned for one or more of the Inserting, Dosing and Testing Periods. Thus, a Testing Pressure Max is a pressure which cannot be exceeded during the Testing Period or the test will be aborted.

In another aspect, a pressure below the maximum may also serve as a threshold pressure. For example, a Pressure Limit may be assigned to a pressure that may trigger certain responses. A Pressure Limit may be used to signal the user that a significant pressure has been applied to the test strip. This may be useful in educating the user as to the risk of having excessive pressure applied to the test strip during testing, and a warning to that effect could be displayed to the user. Also, a Pressure Limit may be considered in combination with other sensed conditions such that a test may be aborted even though the Pressure Max has not been achieved. As previously indicated, a separate Pressure Limit may be assigned for various times during testing, including separately for each test period.

In some instances, there may be some amount of base pressure which is present even without pressure being applied externally to the sample end of the test strip. A determination can be made as to this base pressure, e.g., by noting a steady-state pressure following initial insertion of the test strip into the meter. The pressure applied to the sample end of the test strip may then be determined based upon changes from the base pressure. In one embodiment, the base pressure is equal or close to zero pressure. In that manner, any pressure applied against the sensor can be assumed to be pressure applied against the dosing end of the test strip.

The processor is responsive to any sensed pressure in order to receive the pressure from the sensor, to compare the sensed pressure to a pressure threshold value, and to indicate when the sensed pressure exceeds the pressure threshold value. In one embodiment, an Absolute Pressure Max is assigned and stored in the memory of the controller and the pressure applied to the test strip is determined as the pressure applied by the test strip relative to the meter. The processor senses the pressure at predetermined times and indicates if the sensed pressure ever exceeds the Absolute Pressure Max. Additionally, various pressure thresholds may be assigned and stored in memory for a variety of amounts, times and durations. The processor again senses the pressure and compares it to a pressure threshold correlated to the time the pressure is sensed.

If the sensed pressure exceeds a threshold pressure, this condition may be indicated in a variety of ways. The controller is operatively coupled with the processor to receive the indications from the processor. In response to the indication by the processor, the controller may effectuate correlated actions. One form of response is to generate a user-detectable signal indicating the condition represented by the sensed pressure. This signal may take the form of a visible signal such as a light or a message on the meter. The signal may also comprise a text or other form of message delivered apart from the meter. Alternative forms of signal include audible or tactile (including vibratory) signals. Such user-detectable signals may be varied based on the severity of the sensed pressure.

For specified pressure conditions, the controller operates to terminate a test. Thus, if an Absolute Pressure Max is exceeded, then the meter will terminate the test and provide a readout indicating that the test has been terminated due to the application of undue pressure to the test strip. This acts as a failsafe that prevents the user from relying on a potentially erroneous test result, and further serves to educate the user to the problem of excess pressure on the test strip.

Pressure sensors useful in accordance with the present invention are readily available. Such pressure sensors typically comprise small, inexpensive microchips. These may be directly useful in a given meter, or readily adapted to such use. Examples of pressure sensors useful with the present invention include square force-sensitive resistors (FRS), robbon soft pots, or capacitive touch pads.

The pressure thresholds may be determined in a variety of ways. For example, tests are conducted which simulate the application of pressure against the sample end of a test strip while it is received within a meter for testing. Standard test samples at known analyte concentrations are used. The tests are conducted with varying levels of pressure and the concentration determinations are compared to the known value. By assessing the occurrence of erroneous results, a pressure threshold can be determined. Testing may be performed by applying pressures in different orientations in order to identify corresponding pressure thresholds. Similarly, the pressures are applied at different times during the test in order to establish pressure thresholds based on the time the pressure is applied.

As a further example, a study was conducted to determine the occurrence of pressure-related errors for a specific type of meter and test strip. In the study, people were asked to dose strips properly (i.e., with slight touching to the end of the strip) and the pressure information was collected for each measurement. Based on the data, a proper threshold amount was determined. Once the threshold was set, any pressure value that exceeds the threshold is flagged to be the result of a bad dosing technique and no analyte measurement is provided. Instead, the meter provides an error message and causes the user to test again to properly obtain an analyte measurement.

In other embodiments, the empirical data from a multitude of use cases may be compiled in order to determine a cause and effect between any applied pressure—whether or not deemed an 'undue pressure'—and a degree or amount of bias introduced in the test result. By correlating the amount of applied pressure with a degree or amount of introduced bias, a distinct correction factor or algorithm can be identified. This factor or algorithm may then be implemented to further adjust a measurement test result accordingly without requiring the primary measurement algorithm for the test to account for such bias. In this way, the primary measurement algorithm may remain focused and optimized with respect to data directly relating to the testing sequence, signals, and signal responses.

The invention claimed is:

1. A meter for detecting a presence and/or concentration of an analyte in a liquid biological sample, the meter using a test strip inserted into the meter for detecting the analyte, the meter comprising:
   a housing defining an opening communicating with an internal cavity adapted to receive at least a portion of the test strip, the test strip being configured to retain the liquid biological sample;
   a pressure sensor arranged and configured to sense a pressure exerted by the inserted test strip relative to said housing; and
   a controller configured to detect a presence and/or concentration of an analyte in the liquid biological sample using the test strip, said controller comprising a processor and a memory, wherein the memory is configured to store one or more predetermined pressure threshold values, the processor responsive to said pressure sensor and configured to:
   receive signals corresponding to the sensed pressure from said sensor;
   compare the signals to a pressure threshold value, and
   indicate when the sensed pressure exceeds the pressure threshold value.

2. The meter of claim 1 in which the pressure sensor is arranged and configured to sense pressure exerted in a direction longitudinal of the orientation of an inserted test strip.

3. The meter of claim 1 in which the memory is configured to store a maximum pressure threshold and the processor is configured to indicate when the sensed pressure exceeds the maximum pressure threshold.

4. The meter of claim 3 in which said pressure sensor is configured to sense pressure over a predetermined period of time, and in which the processor is configured to indicate if the sensed pressure ever exceeds the maximum pressure threshold during the predetermined period of time.

5. The meter of claim 4 in which the predetermined period of time is at least one of the insertion period, the dosing period and the testing period.

6. The meter of claim 1 in which said pressure sensor is configured to sense pressure over a predetermined period of time, and in which the processor is configured to indicate if the sensed pressure ever exceeds the pressure threshold value during the predetermined period of time.

7. The meter of claim 6 in which the predetermined period of time is at least one of the insertion period, the dosing period and the testing period.

8. The meter of claim 7 in which the predetermined period of time is the dosing period.

9. The meter of claim 1 in which the processor is configured to provide an indication of excessive pressure in the form of a user-detectable signal.

10. The meter of claim 9 in which the user-detectable signal is selected from the group consisting of an audible, visual or tactile signal.

11. The meter of claim 10 in which the user-detectable signal is variable based on the severity of the sensed pressure.

12. The meter of claim 1 in which the processor is configured to terminate a meter test if the sensed pressure exceeds the pressure threshold value.

13. The meter of claim 1 and further including a second pressure sensor arranged and configured to sense a pressure exerted by an inserted test strip relative to said housing, said second pressure sensor being configured to sense a pressure which is exerted in a direction different from the direction of pressure sensed by the first sensor.

14. The meter of claim 1 configured to detect the analyte using a test strip selected from the group consisting of an electrochemical test strip and an optical test strip.

15. The meter of claim 14 configured to detect the analyte using a test strip selected from the group consisting of a colorimetric test strip and a photometric test strip.

16. The meter of claim 1 in which the pressure sensor is arranged and configured to sense a pressure applied to the dosing end of the test strip.

17. The meter of claim 1 in which the pressure sensor is arranged and configured to sense a pressure applied to the test strip by the user of the meter.

18. A method for detecting the application of an undue pressure applied against a test strip relative to a meter, the meter being for determining a presence and/or concentration of an analyte in a liquid biological sample using the test strip, the method comprising:
  receiving at least a portion of the test strip within the meter in a position adjacent a pressure sensor arranged and configured to sense a pressure exerted by the inserted test strip relative to the meter;
  using the sensor to sense the pressure applied by the inserted test strip relative to the meter; and
  comparing the sensed pressure to a predetermined pressure threshold value.

19. The method of claim 18 and which further comprises providing an indication when the sensed pressure exceeds the pressure threshold value.

20. The method of claim 19 in which the indication is in the form of a user-detectable signal.

21. The method of claim 20 in which the user-detectable signal is selected from the group consisting of audible, visual or tactile signals.

22. The method of claim 20 in which the user-detectable signal is variable based on the severity of the sensed pressure.

23. The method of claim 19 in which the indication is a termination of the test for determining a presence and/or concentration of an analyte.

* * * * *